United States Patent

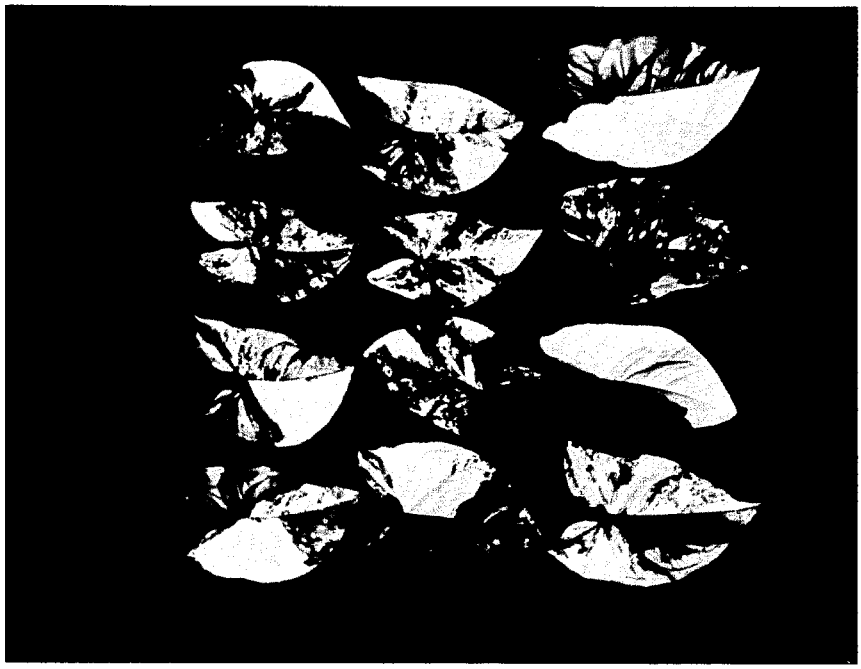
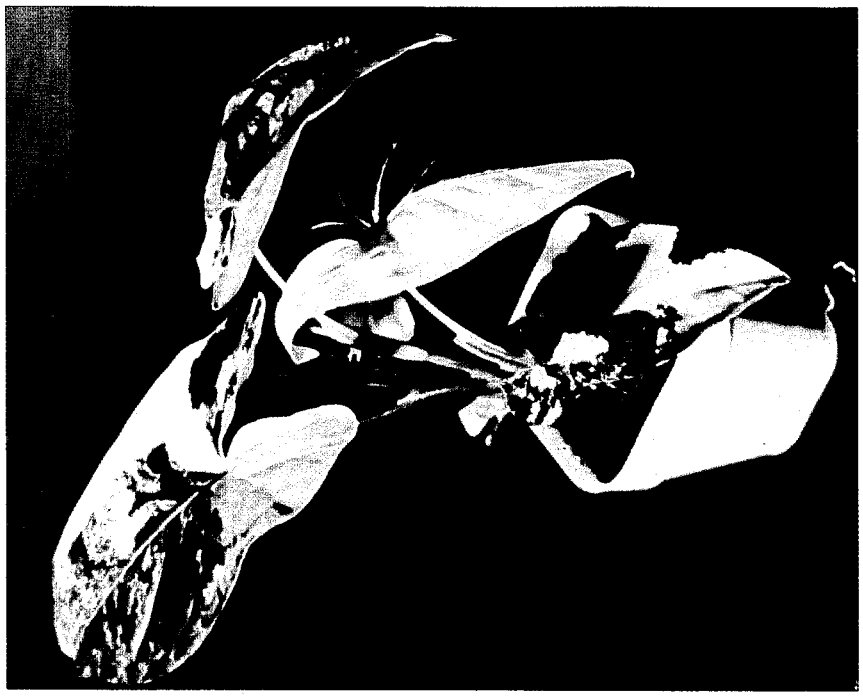

Plant Pat. 3,961

Patented Oct. 19, 1976

3,961

SYNGONIUM PLANT

Theodore R. Quay, Jr., Upland, Calif., assignor to Quay Nurseries, Ontario, Calif.

Filed July 29, 1975, Ser. No. 600,108

Int. Cl.[2] A01H 5/00

U.S. Cl. Plt.—88 1 Claim

The present invention relates to a new and distinct variety of Syngonium plant which was discovered by me as a cultivated seedling in a greenhouse on my nursery property formerly located in Chino, Calif.

At the time of my discovery, I was growing in my nursery greenhouse aforesaid a large block of Syngonium plants of the variety known as "Emerald Gem" (unpatented) derived from seeds which I had obtained in Mexico and then planted in my nursery. During my cultivation and care of these seedling plants, my attention was first attracted to one particular plant which bore leaves of unusual color and color patterns. I carefully preserved this plant and kept it under close observation. As it continued to grow, many other distinctive and attractive color patterns appeared, so I took stem and eye cuttings therefrom and from successive progeny thereof through six generations (now in the seventh propagation) which I propagated in my greenhouses.

Continued and prolonged observations of the original seedling and its progeny derived therefrom as aforementioned, have convinced me that it is a new and improved variety which is distinguished from its parent variety "Emerald Gem," as well as from all other varieties of which I am aware, as particularly evidenced by the following unique combination of principal characteristics which are outstanding therein:

(1) A size, shape and habit of growth generally resembling the variety "Emerald Gem," with the foliage coloring resembling the variety "Golden Pothos" (unpatented) but distinctly different therefrom in color patterns; and (2) Distinctive, attractive and sharply contrasting variegated leaf color patterns extending over leaf areas ranging from mostly dark to light green colors on same leaves and mostly or entirely gold to light cream or ivory colors on ther leaves, or mixtures of all these colors in random patterns of various shapes and size on still other leaves.

The accompanying drawing shows a typical young specimen plant of my new Syngonium variety, as well as a group of typical leaf specimens illustrating typical color patterns of random leaves, as depicted in color as nearly true as it is reasonably possible to make the same in a color illustration of this character.

The following is a detailed description of my new Syngonium variety, with color terminology in accordance with Koster's Color Guide, except where general color terms of ordinary dictionary significance are obvious:

Parentage: Seedling mutation of "Emerald Gem" which bears green leaves.

Propagation: Holds its dinstinguishing characteristics through succeeding propagations by cutting and layering.

Locality where grown and observed: Chino and Upland, Calif.

Plant:

*Form.*—Creeping and hanging vine; suitable for potting, for large totem poles and for hanging baskets.

*Growth.*—Slender; bending; vigorous; robust; creeping; will attain a length of 20 feet or more if not disturbed or cut back.

*Roots.*—Medium size root system; no tubers; will root from leaf joints on the vine and will cling to moist materials.

*Stem.*—Size—from 1/8 inch to 1/4 inch in diameter.

*Internodes.*—From 1 3/4 inches to 2 inches in average length.

Foliage:

*Size.*—Medium to large. Length—from about 3 1/2 inches to 6 inches. Width—from about 2 inches to 3 inches.

*Quantity.*—Abundant.

*Shape.*—From oval-pointed to arrow-head or lanceolate.

*Texture.*—Upper side—smooth. Underside—slightly rough.

*Color.*—Some leaves are mostly or entirely green, with the green color ranging from near Taxus Green, Plate No. 81 or darker, to near Moss Green, Plate No. 76 or lighter; other leaves are half green and half light lemon yellow to ivory on respective opposite sides of midrib; still other leaves have light golden yellow to ivory blotches of varying shapes and sizes on one or the other sides of the midrib or variegated over entire leaf surface in irregular patterns, with yellow colors ranging from near Cream Yellow, Plate No. 4 to near Creamy White, Plate No. 2.

*Veins.*—Fairly prominent; slightly recessed on upper surface and slightly protruding on under surface.

*Petioles.*—Length—from about 4 inches to 6 inches. Diameter—from about 1/8 to 3/16 inch. Color—near Boxwood Green, Plate No. 79, becoming somewhat reddish toward base.

Flowers: None.

Disease resistance: Good, as determined from comparision with other varieties grown under the same conditions at Chino and Upland, Calif.; comparable to that of parent variety "Emerald Gem"; no diseases have appeared to date during propagations through seven generations.

General observations: My new variety of Syngonium plant is unique and distinct from all other varieties of which I am aware, due primarily to the extensive, interesting and attractive variegated color patterns of its leaves, as distinguished from the overall, solid dark green leaf color of its parent variety "Emerald Gem." In most other standard Syngonium varieties, such as "Roxanne," "Imperial White" and "Noack White" (all unpatented), any leaf color variegations present are in the form of narrow pale green to light greenish white stripes which are quite narrow and are confined to the midrib and/or vein areas of the leaves, and therefore are not very prominent. In these standard varieties, the leaves are largely medium green to bluish dark green in color, and for the most part are smaller in size than the leaves of my new variety.

I claim:

1. A new and distinct variety of Syngonium plant, substantially as herein shown and described, characterized particularly as to novelty by the unique combination of a size, shape and habit of growth generally resembling the variety "Emerald Gem," with the foliage coloring resembling the variety "Golden Pothos" (unpatented) but distinctly different therefrom in color patterns, and distinctive, attractive and sharply contrasting variegated leaf color patterns extending over leaf areas ranging from mostly dark to light green colors on some leaves and mostly or entirely gold to light cream or ivory colors on other leaves, or mixtures of all these colors in random patterns of various shapes and size on still other leaves.

No references cited.

ROBERT E. BAGWILL, Primary Examiner